United States Patent [19]
Hirano et al.

[11] Patent Number: 5,683,685
[45] Date of Patent: Nov. 4, 1997

[54] HAIR COSMETIC COMPOSITION

[75] Inventors: Yuji Hirano; Aya Hirano, both of Chiba; Naohisa Kure, Tokyo, all of Japan

[73] Assignee: Kao Corporation, Tokyo, Japan

[21] Appl. No.: 676,225

[22] PCT Filed: Jan. 25, 1995

[86] PCT No.: PCT/JP95/00084

§ 371 Date: Jul. 23, 1996

§ 102(e) Date: Jul. 23, 1996

[87] PCT Pub. No.: WO95/20375

PCT Pub. Date: Aug. 3, 1995

[30] Foreign Application Priority Data

Jan. 27, 1994 [JP] Japan ..................................... 6-007459

[51] Int. Cl.$^6$ .................................................. A61K 31/74
[52] U.S. Cl. .......................... 424/78.03; 424/47; 424/70; 424/78.31
[58] Field of Search ........................... 424/47, 70, 78.03, 424/78.31

[56] References Cited

U.S. PATENT DOCUMENTS 5,240,695  8/1993  Dubief et al. ............................. 424/47

FOREIGN PATENT DOCUMENTS 0529437  3/1993  European Pat. Off. .

Primary Examiner—Terressa Mosley
Attorney, Agent, or Firm—Oblon, Spivak, McClelland, Maier & Neustadt, P.C.

[57] ABSTRACT

The present invention provides a hair cosmetic composition containing the following components (A), (B), (C), and (D):
(A) an organic solvent,
(B) a naphthalene sulfonic acid and/or a benzophenone sulfonic acid,
(C) an anionic surfactant and/or an amphoteric surfactant, and
(D) an oily agent.

The hair cosmetic composition of the invention imparts satisfactory firmness/elasticity to hair in a short time, holds the firmness/elasticity for a long time, and provides the hair with excellent conditioning effects.

11 Claims, No Drawings

HAIR COSMETIC COMPOSITION

This application is a 371 of PCT/JP95/0084.

TECHNICAL FIELD

The present invention relates to a hair cosmetic composition which imparts satisfactory firmness/elasticity to hair fibers in a short time, which holds the firmness/elasticity for a long time, and which at the same time provides the hair with conditioning effects.

BACKGROUND ART

Not a few complaints about the hair are caused from the low elasticity of hair fibers such as lack of firmness/elasticity and less volume. In order to meet the needs of people having such complaints, a variety of hair treatment compositions have heretofore been proposed which contain components for providing firmness/elasticity and components with conditioning effects. A majority of them exhibit their effects when they are adsorbed onto the surfaces of hair fibers, but the adsorbed compositions are rinsed off upon shampooing. Therefore, repeated treatments are needed, which is not convenient. Separately, attempts have been made to obtain an effect by permeating a hair treatment composition into hair fibers. However, the permeability of the composition is poor and requires a prolonged time for treatment while producing only an insufficient effect.

Hair treatment compositions proposed by EP-A-0529437 comprise an organic solvent and an aromatic sulfonic acid. Although this composition imparts firmness/elasticity to hair fibers in a short time and the effects of the composition are long-lasting, the conditioning effects of the composition such as providing moistness, smoothness, etc. to hair fibers are still unsatisfactory.

Accordingly, hair cosmetic compositions capable of imparting firmness/elasticity to hair fibers in a short time, holding the firmness/elasticity for a long time, and providing the hair with satisfactory conditioning effects are still desired.

DISCLOSURE OF THE INVENTION

Accordingly, the present invention provides a hair cosmetic composition which comprises the following components (A), (B), (C), and (D):

(A) an organic solvent, (B) a naphthalene sulfonic acid and/or a benzophenone sulfonic acid, (C) an anionic surfactant and/or an amphoteric surfactant, and (D) an oily agent.

According to the present invention, satisfactory firmness/elasticity can be given to hair fibers through a short-term treatment due to the incorporation of an organic solvent, a naphthalene sulfonic acid and/or a benzophenone sulfonic acid, an anionic surfactant and/or an amphoteric surfactant, and an oily agent, and the effects obtained are long-lasting. In addition, conditioning effects can also be given to the hair.

BEST MODE FOR CARRYING OUT THE INVENTION

The organic solvent which is used in the present invention as component (A) is compatible with water. Examples of the organic solvent (A) include the compounds of the following formula (1), N-alkylpyrrolidones of the following formula (2), and C1-C4 alkylene carbonates.

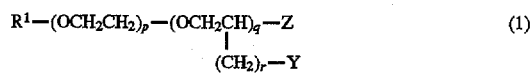

wherein $R^1$ represents hydrogen, lower alkyl, or a group

(wherein $R^2$ represents hydrogen, methyl, or methoxy, $R^3$ represents a direct bond or a C1-C3 saturated or unsaturated divalent hydrocarbon group), Y and Z each represents hydrogen or hydroxy, p, q, and r are integers of from 0 to 5, with the exception of the cases where p=q=r=0 and Z=H; and p=q=r=0, $R^1$=H, and Z=OH.

wherein $R^4$ represents C1-C18 linear or branched alkyl.

Among the above-described species of component (A), the aromatic alcohols of the following formula (3) are especially preferred.

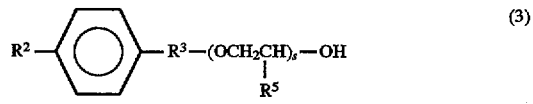

wherein $R^5$ is hydrogen or methyl, s is an integer from 0 to 5 inclusive, and $R^2$ and $R^3$ have the same meaning as described above with the exception that $R^3$ is not a direct bond if s is equal to 0.

Specific examples of the organic solvent (A) include ethanol, isopropanol, n-propanol, n-butanol, isobutanol, ethylene glycol, propylene glycol, 1,3-butanediol, benzyl alcohol, cinnamyl alcohol, phenethyl alcohol, p-anisyl alcohol, p-methylbenzyl alcohol, phenoxy ethanol, phenoxy isopropanol, 2-benzyloxyethanol, methyl carbitol, ethyl carbitol, propyl carbitol, butyl carbitol, triethylene glycol monoethylether, triethylene glycol monobutyl ether, glycerol, N-methylpyrrolidone, N-octylpyrrolidone, N-laurylpyrrolidone, ethylene carbonate(1,3-dioxolan-2-one), propylene carbonate(4-methyl-1,3-dioxolan-2-one), butylene carbonate(4-ethyl-1,3-dioxolan-2-one), etc. They are used singly or in combinations of two or more.

Of these compounds, aromatic alcohols of formula (3) are especially preferred. Specifically, benzyl alcohol, cinnamyl alcohol, phenethyl alcohol, p-anisyl alcohol, p-methylbenzyl alcohol, phenoxy ethanol, phenoxy isopropanol, 2-benzyloxyethanol are preferred with benzyl alcohol, p-methylbenzyl alcohol, 2-benzyloxyethanol, phenoxy ethanol, and phenoxy isopropanol being particularly preferred.

The organic solvent (A) is preferably incorporated in the hair cosmetic composition of the invention in an amount of from 0.5 to 50% by weight (hereinafter simply referred to as %) based on the total amount of the composition. If the amount of the organic solvent (A) is in the range from 2 to 30%, or particularly from 5 to 25%, prominent effects can be obtained with favorable sensation and thus preferable. The proportion between water and the organic solvent depends on the solubility of the solvent in water. Generally, the proportion of the amount of the organic solvent to that of water is preferably from 10:90 to 50:50.

Of the species of component (B) which are used in the present invention, examples of the naphthalene sulfonic acid include the compounds represented by the following formula (4):

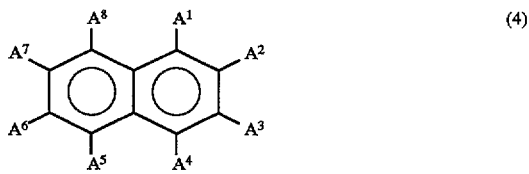
(4)

wherein one or more of $A^1$ to $A^8$ represent a sulfonic group or a salt thereof, and the remaining group(s) represent(s) hydrogen, halogen, hydroxy, nitro, carboxy, lower alkoxycarbonyl, alkyl, alkenyl, lower alkoxy, formyl, acyl, phenylazo or substituted phenylazo, or a group

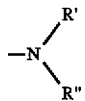

wherein R' and R" represent hydrogen, lower alkyl, lower alkenyl, phenyl, benzyl, or acyl.

In the above formula (4), examples of the alkyl include C1-C18 alkyl, examples of the alkenyl include C2-C18 alkenyl, examples of the lower alkyl and lower alkoxy include those of C1-C6, and examples of the lower alkenyl include C2-C6 alkenyl. Examples of the acyl include C2-C6 alkanoyl; examples of substituted or unsubstituted phenylazo include phenylazo, carboxyphenylazo, etc; examples of the halogen include fluorine, chlorine, bromine, and iodine. It is preferred that one or two of the $A^1$ to $A^8$ of the formula (4) be sulfonic acid or a salt thereof. Examples of the salt of sulfonic acid include alkaline metal salts such as a sodium salt, potassium salt, etc., ammonium salts, and quaternary ammonium salts.

Specific examples of the naphthalene sulfonic acid include 1- or 2- naphthalene sulfonic acid, 1,3-naphthalenedisulfonic acid, 1,7-naphthalenedisulfonic acid, 2,7-naphthalenedisulfonic acid, 1,5-naphthalenedisulfonic acid, 2,6-naphthalenedisulfonic acid, 1,3,6-naphthalenetrisulfonic acid, 1-naphthol-2-sulfonic acid, 1-naphthol-4-sulfonic acid, 2-naphthol-6-sulfonic acid, 2-naphthol-7-sulfonic acid, 1-naphthol-3,6-disulfonic acid, 2-naphthol-3,6-disulfonic acid, 2-naphthol-6,8-disulfonic acid, 2,3-dihydroxynaphthalene-6-sulfonic acid, 1,7-dihydroxynaphthalene-3-sulfonic acid, chromotoropic acid (4,5-dihydroxynaphthalene-2,7-disulfonic acid), 3,6-dihydroxynaphthalene-2,7-disulfonic acid, S acid (1-amino-8-naphthol-4-sulfonic acid), gamma acid (2-amino-8-naphthol-6-sulfonic acid), J acid (2-amino-5-naphthol-7-sulfonic acid), H acid (1-amino-8-naphthol-3,6-disulfonic acid), 7-amino-1,3-naphthalenedisulfonic acid, 1-amino-2-naphthol-4-sulfonic acid, 1-naphthylamine-4-sulfonic acid, Broenner's acid (2-naphthylamine-6-sulfonic acid), Cleve's acid (1-naphthylamine-7-sulfonic acid), 2-naphthylamine-1-sulfonic acid, 1-naphthylamine-6-sulfonic acid, 1-naphthylamine-8-sulfonic acid, 4-amino-5-hydroxy-8-phenylazo-2,7-naphthalenedisulfonic acid, 4-amino-8-(4-carboxyphenylazo)-5-hydroxy-2,7-naphthalenedisulfonic acid, 6-amino-4-hydroxy-3-phenylazo-2-naphthalenesulfonic acid, 4-amino-8-(4-carboxyphenylazo)-5-hydroxy-1-naphthalenesulfonic acid, 7-amino-4-hydroxy-1-phenylazo-2-naphthalenesulfonic acid, 8-amino-5-(4-carboxyphenylazo)-2-naphthalenesulfonic acid, 4-amino-3-(4-carboxyphenylazo)-5-hydroxy-1-naphthalenesulfonic acid, 6-amino-4-hydroxy-5-phenylazo-2-naphthalenesulfonic acid, 2,7-diamino-1-naphthol-3-sulfonic acid, 7,8-diamino-1-naphthol-3-sulfonic acid, naphthalenesulfonic acid - formalin polycondensation product (weight-average degree of polycondensation: 2–100), 6-methyl-2-naphthalenesulfonic acid, 4-ethyl-1-naphthalenesulfonic acid, 5-isopropyl-1-naphthalenesulfonic acid, 5-butyl-2-naphthalenesulfonic acid, and their salts. Of these, particularly preferred are 1-naphthalenesulfonic acid, 2-naphthalenesulfonic acid, 1,5-naphthalenedisulfonic acid, 2,6-naphthalenedisulfonic acid, 2,7-naphthalenedisulfonic acid, 1,3-naphthalenedisulfonic acid, H acid (1-amino-8-naphthol-3,6-disulfonic acid), 1,3,6-naphthalenetrisulfonic acid, chromotoropic acid, and naphthalenesulfonic acid - formalin polycondensation product (weight-average degree of polycondensation: 2–100), and their salts.

Of the species of component (B), examples of the benzophenonesulfonic acid include those of the following formula (5):

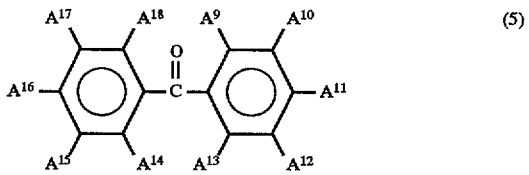
(5)

wherein one or more of $A^9$ to $A^{18}$ represent a sulfonic group or a salt thereof, and the remaining group(s) represent(s) hydrogen, halogen, hydroxy, carboxy, lower alkyl, lower alkenyl, lower alkoxy, or acyl.

In the above formula (5), the lower alkyl and the lower alkoxy include those having 1 to 6 carbon atoms; and the lower alkenyl includes those having 2 to 6 carbon atoms. Examples of the acyl include a C2-C6 alkanoyl. Examples of the halogen include fluorine, chlorine, bromine, and iodine. It is particularly preferred that one or two of the $A^9$ to $A^{18}$ of the formula (5) be sulfonic acid or a salt thereof. Examples of the salt of sulfonic acid include alkaline metal salts such as a sodium salt, potassium salt, etc., alkaline earth metal salts such as a calcium salt, ammonium salts, and quaternary ammonium salts.

Specific examples of the benzophenonesulfonic acid include oxybenzonesulfonic acid, dihydroxydimethoxybenzophenonedisulfonic acid, dihydroxydimethoxybenzophenonesulfonic acid, dihydroxydimethoxybenzophenonedisulfonic acid, o-chlorobenzophenonesulfonic acid, p-chlorobenzophenone-sulfonic acid, 4,4'-dichlorobenzophenonesulfonic acid, 2,4-dichlorobenzophenonesulfonic acid, 2,4-dichlorobenzophenonesulfonic acid, 2-hydroxybenzophenonesulfonic acid, 4-hydroxybenzophenonesulfonic acid, 2-aminobenzophenonesulfonic acid, 4-aminobenzophenonesulfonic acid, 2-methylbenzophenonesulfonic acid, 4-methoxybenzophenonesulfonic acid, 4,4'-dimethylbenzophenonesulfonic acid, 4,4'-dimethoxybenzophenonesulfonic acid, 4-chloro-4'-hydroxybenzophenonesulfonic acid, and their salts. Of these, particularly preferred are oxybenzonesulfonic acid, dihydroxymethoxybenzophenonedisulfonic acid, dihydroxydimethoxybenzophononesulfonic acid, dihydroxydimethoxybenzophenonedisulfonic acid, and their salts.

The naphthalenesulfonic acids and the benzosulfonic acids, which are component (B), are used singly or in combinations of two or more. They are preferably incorporated in the hair cosmetic composition of the invention in an amount from 0.1 to 10% by weight based on the total amount of the composition. If the amount is in the range from 0.5 to 5%, or particularly from 1.0 to 3.0%, excellent firmness/ elasticity can be imparted to the hair without impeding the feel to the touch of the hair, and thus preferable.

Of the species of component (C) which are used in the present invention, examples of the anionic surfactant include the following compounds.

(1) Linear or branched alkylbenzene sulfonates having an alkyl group containing 10 to 16 carbon atoms on average.
(2) Alkyl or alkenyl ether sulfates having a linear or branched alkyl or alkenyl group containing 10 to 20 carbon atoms on average and a polyether chain to which 0.5 to 8 moles on average of ethylene oxide, propylene oxide, butylene oxide, or a combination of two or more of these is added per 1 molecule of sulfate.
(3) Alkyl or alkenyl sulfates having an alkyl or alkenyl group containing 10 to 20 carbon atoms on average.
(4) Olefin sulfonates having 10 to 20 carbon atoms on average per molecule.
(5) Alkane sulfonates having 10 to 20 carbon atoms on average per molecule.
(6) Saturated or unsaturated fatty acid salts having 10 to 24 carbon atoms on average per molecule.
(7) Alkyl or alkenyl ether carboxylates having an alkyl or alkenyl group containing 10 to 20 carbon atoms on average and a polyether chain to which 0.5 to 8 moles on average of ethylene oxide, propylene oxide, butylene oxide, or a combination of two or more of these is added per 1 molecule of carboxylate.
(8) Alpha-sulfofatty acid salts or esters having an alkyl or alkenyl group containing 10 to 20 carbon atoms on average per molecule.
(9) N-acyl amino acid-type surfactants having a C8-C24 acyl group, a free carboxylic residue, or a sulfonic residue.
(10) Phosphoric mono- or di- ester-type surfactants having C8-C24 alkyl or alkenyl, or their ethoxylates.
(11) Sulfosuccinic esters derived from a higher aliphatic amide or a C8-C22 higher alcohol or its ethoxylates.
(12) Sulfonic acid salts of C8-C20 higher fatty aid monoethanolamides, diethanolamides or their ethoxylates.
(13) Sulfonic acid salts of C8-C20 monoglycerides.
(14) Salts of C8-C20 higher fatty acids and isethionic acid.

Of the species of component (C), examples of the amphoteric surfactant include the following compounds.

(1) Imidazolines having C8-C24 alkyl, alkenyl or acyl, and of an alpha- adduct type, secondary amide type, or a tertiary amide type.
(2) Carbobetaines, amidebetaines, sulfobetaines, hydroxysulfobetaines, and amidesulfobetaines having C6-C24 alkyl, alkenyl or acyl.
(3) Amineoxides having C6-C24 alkyl or alkenyl.

Among the above surfactants, the compounds (a) to (f) below are particularly preferred.

(a) N-acyl-L-glutamic acids and their salts represented by the following formula (6):

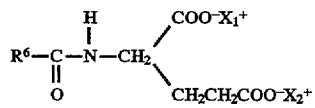

wherein $R^6$ is C12-C18 linear or branched alkyl or alkenyl, $X_1$ and $X_2$ are hydrogen, potassium, sodium, or a triethanolamine salt, with $X_1$ and $X_2$ being not necessarily identical.

(b) N-acyl-N-methyl-beta-alanines and their salts represented by the following formula (7):

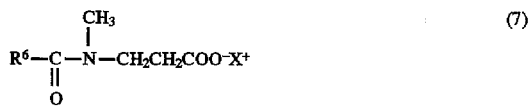

wherein $R^6$ has the same meaning as defined above, X is hydrogen, potassium, sodium, or a triethanolamine salt.

(c) Aminoalkyltaurinic acids and their salts represented by the following formula (8):

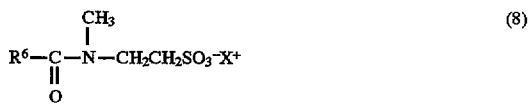

wherein $R^6$ and X have the same meaning as defined above.

(d) Amide ether sulfates and their salts represented by the following formula (9):

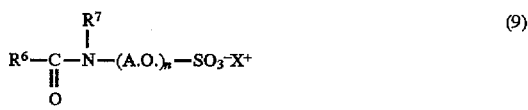

wherein $R^6$ is C12-C18 linear or branched alkyl or alkenyl, $R^7$ is C1-C3 linear alkyl, $(A.O.)_n$ is 1 to 5 moles on average (=n) of ethylene oxide, propylene oxide, or butylene oxide (A.O.) which has been added, and $R^6$ and X have the same meaning as defined above.

(e) Monoalkyl or dialkyl phosphoric acids and their salts represented by the following formula (10):

wherein $R^8$ is C12-C18 linear or branched alkyl or alkenyl, and $R^6$ and X have the same meaning as defined above (if $R^8$ is hydrogen, the formula (10) represents monoalkyl phosphoric acids and their salts).

(f) Secondary amide- or tertiary amide-type imidazoline amphoteric surfactants and their salts represented by the following formulas (11), (12), and (13):

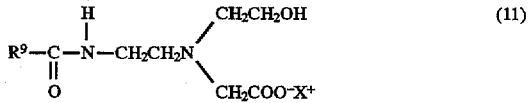

wherein $R^9$ is C7-C18 linear or branched alkyl or alkenyl, and X has the same meaning as defined above;

wherein $R^9$ and X have the same meaning as defined above;

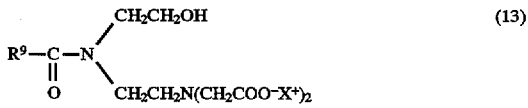

wherein $R^9$ and X have the same meaning as defined above.

(g) Carbobetaine-type, sulfobetaine-type, and hydroxysulfobetaine-type amphoteric surfactants represented by the following formulas (14) and (15):

wherein $R^{10}$ is C6-C24 alkyl, alkenyl, or acyl;

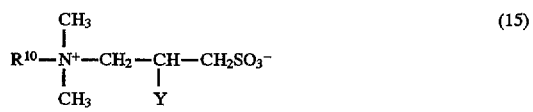

wherein Y is hydrogen or hydroxyl, and $R^{10}$ has the same meaning as defined above.

These anionic and amphoteric surfactants are used singly or in combinations of two or more. They are preferably incorporated in an amount of from 0.1 to 25% based on the total amount of the composition. If the amount falls in a range from 0.5 to 15%, and in particular from 1.0 to 10%, excellent feel to the touch can be obtained and thus preferable.

Examples of the oily agent, component (D), include various oils and fats and hydrocarbons which are either liquid or solid.

Examples of the oils and fats include C12-C30 saturated or unsaturated alcohols; ethers of these alcohols and polyhydric alcohols; esters of these alcohols and C1-C11 fatty acids; C12-C30 saturated or unsaturated fatty acids; esters of these fatty acids and monohydric or polyhydric alcohols; amides of these fatty acids and amines; sterols; squalenes; phospholipids; glycolipids; oils or fats of animal origin; and oils or fats of vegetable origin.

Examples of the C12-C30 saturated or unsaturated alcohols include n-dodecal, myristyl alcohol, cetyl alcohol, stearyl alcohol, oleyl alcohol, octyldodecanol, behenyl alcohol, ceryl alcohol, myricyl alcohol, caranabyl alcohol, arachin alcohol, and the like. Examples of the polyhydric alcohols which can form ethers with these alcohols include glycerol and polyalkylene glycol, and examples the formed ethers include alpha-monoisostearyl glyceryl ether, polyoxyethylene polyoxypropylene stearyl ether, polyoxyethylene cetyl ether, polyoxyethylene octyldodecyl ether, and the like. Examples of the esters of these alcohols and C1-C11 fatty acids include cetyl 2-ethylhexanoate, diisostearyl malate, and the like.

Examples of the C12-C30 saturated or unsaturated fatty acids include lauric acid, myristic acid, 18-methyleicosanoic acid, palmitic acid, stearic acid, isostearic acid, behenic acid, cerotic acid, palm oil fatty acid, oleic acid, etc. Examples of the monohydric or polyhydric alcohols which can form esters with these fatty acids include the aforementioned C12-C30 saturated or unsaturated alcohols, glycerols, sterols, and fat-soluble vitamins, and examples of the formed esters include oleic monoglycerides, palmitic monoglycerides, behenic monoglycerides, myristic monoglycerides, isostearic monoglycerides, isostearic diglycerides, polyoxyethylene glyceryl monoisostearates, isopropyl myristates, cholesteryl ester isostearates, dipentaerythritol fatty acid esters. Examples of the amides of these fatty acids and amines include aliphatic dialkylaminoalkylamides (long chain amideamines), and specifically, diethylaminoethylamide stearate (Amideamine S by Kao Corp.).

Specific examples of the phospholipids include soybean phospholipids, and specific examples of the glycolipids include sophorose lipids (Glycolipid PSL by Kao Corp.). Specific examples of the oils and fats of animal or vegetable origin include mink oil, olive oil (the major component is glycerol oleate), beeswax (the major component is myricyl alcohol palmitate), palm oil (the major component is glycerol myristate), whale wax (the major component is ceryl alcohol palmitate), and lanolin.

Examples of the hydrocarbons include Vaseline, liquid paraffin, solid paraffin, etc.

Of these oily agents, especially preferred are higher alcohols having C12-C26 linear or branched alkyl or alkenyl groups.

These oily agents are used singly or in combinations of two or more. They are preferably incorporated in an amount of from 1 to 25% based on the total amount of the composition. If the amount falls in a range of from 3 to 20%, and in particular from 5 to 15%, remarkably satisfactory results can be obtained with excellent feel to the touch of the hair and thus preferable.

When cationic polymers are incorporated into the hair cosmetic composition of the present invention, even more excellent conditioning effects can be obtained without affecting the capability of imparting firmness/elasticity to the hair.

Examples of the cationic polymers include polymers or copolymers of dimethyldiallylammonium chloride; polymers or copolymers of methacrylamide alkyl trimethyl ammonium; cationic cellulose; amino-modified silicone polymers.

The unit structure of the polymers of dimethyldiallyl ammonium chloride is represented by the following formula (16). Preferable examples of monomers which form copolymers along with dimethyldiallylammonium chloride include acrylates, acrylamides, hydroxyethylcellulose, etc.

Specifically, mention may be given to a copolymer of dimethyldiallylammonium chloride and hydroxyethylcellulose which is registered under the name, Polyquaternium-4, in a dictionary of CTFA (The Cosmetic, Toiletry and Fragrance Association, Inc.); a polymer of dimethyldiallylammonium chloride known as Polyquaternium-6; a copolymer of dimethyldiallylammonium chloride with acrylic amide known as Polyquaternium-7; a copolymer of dimethyldiallylammonium chloride with sodium acrylate known as Polyquaternium-22; and a three component-copolymer of dimethyldiallylammonium chloride/acrylic amide/sodium acrylate known as Polyquaternium-39.

The unit structure of the polymers of methacrylamide alkyl trimethyl ammonium is represented by the following formula (17). Among the monomers which form copolymers along with methacrylamide alkyl trimethyl ammonium, vinylpyrrolidone is particularly preferred.

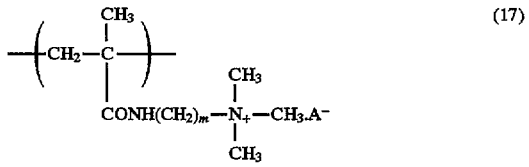

wherein m is an integer of from 1 to 6, and $A^-$ represents an anion).

Specifically, mention may De given to a copolymer of an ethyl sulfuric salt of quaternarized dimethylaminoethyl methacrylate and vinylpyrrolidone which is registered under the name, Polyquaternium-11, in the dictionary of CTFA; a copolymer of methacrylamide propyl trimethyl ammonium with vinylpyrrolidone known as Polyquaternium-28; and a methacrylamide propyl trimethyl ammonium polymer.

Examples of the cationic cellulose include compounds having the unit structure represented by the following formula (18):

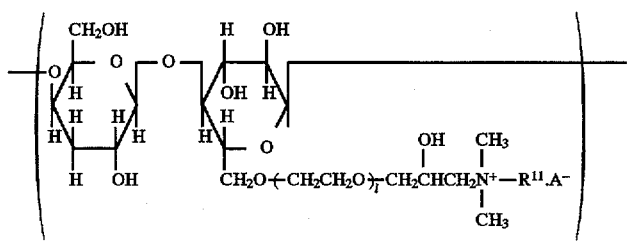

wherein 1 is an integer of from 0 to 10 (preferably from 0 to 5), $R^{11}$ is C1-C18 alkyl, and $A^-$ is an anion.

Specifically, mention may be given to hydroxyethylcellulose registered under the name, Polyquaternium-10, in the dictionary of CTFA; and 2-hydroxypropyl triethyl ammonium chloride ether.

Examples of the amino-modified silicone polymers include polymers of an organosiloxane having at least one aminoalkyl group in the molecule.

The organosiloxane generally contains a methyl group as a functional group in addition to the aminoalkyl group. However, the functional group is not limited only to methyl, and other functional groups may be contained including alkyl groups such as ethyl, propyl, etc.; alkenyl groups such as vinyl, allyl, etc.; aryl groups such as phenyl, naphthyl, etc.; cycloalkyl groups such as cyclohexyl; and other groups such as hydroxy, hydroxyalkyl, hydroxyalkylene, and polyoxyalkylene, etc.

Typical examples of the aminoalkyl groups contained in the amino-modified silicone polymers are those represented by the following formulas (19) or (20):

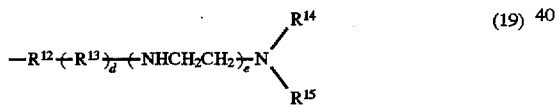

wherein $R^{12}$ represents a divalent hydrocarbon group, $R^{13}$ represents

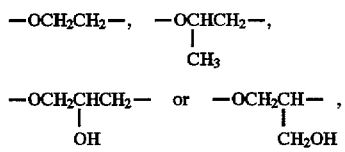

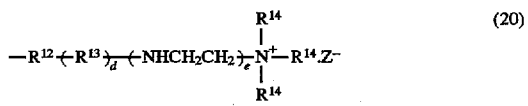

$R^{14}$ and $R^{15}$ represent hydrogen or a monovalent hydrocarbon group, and d and e are integers of from 0 to 6.

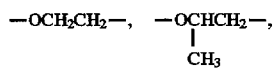

wherein $R^{12}$ represents a divalent hydrocarbon group, $R^{13}$ represents

—OCH$_2$CH$_2$—, —OCHCH$_2$—,
                  |
                  CH$_3$

—OCH$_2$CHCH$_2$—  or  —OCH$_2$CH—,
         |                    |
         OH                   CH$_2$OH $R^{14}$ represents hydrogen or a monovalent hydrocarbon group, d and e are integers of from 0 to 6, and $Z^-$ is a halogen ion or an organic anion.

Examples of the divalent hydrocarbon group represented by $R^{12}$ in formulas (19) and (20) include C1-C6 alkylene groups such as methylene, ethylene, propylene, butylene, and —CH$_2$CH(CH$_3$)CH$_2$—; and C7-C10 alkylenearylene groups such as —(CH$_2$)$_2$—C$_6$H$_4$—. Of these, alkylene groups, particularly propylene, are preferred. Examples of the monovalent hydrocarbon group represented by $R^{14}$ and $R^{15}$ include C1-C18 alkyl or aryl groups such as methyl, ethyl, propyl, hexyl, and phenyl. Both of the groups $R^{14}$ and $R^{15}$ may be hydrogen or a monovalent hydrocarbon group. Alternatively, they may be different in such as a manner that $R^{14}$ is hydrogen and $R^{15}$ is a monovalent hydrocarbon group. Preferable values of d and e are such that d=0 and e=1.

Typically, the hydroxyalkyl group is represented by the following formula:

$$-R^{12}-$$
$$\,\,\,\,\,\,\,\,|$$
$$\,\,\,\,\,\,\,OH$$

wherein $R^{12}$ has the same meaning as defined above.

Typically, the oxyalkyene group and polyoxyalkylene group are represented by the following formula (21):

 (21)

wherein $R^{12}$ has the same meaning as defined above, f is an integer 0 or 1, g is an integer from 1 to 100 inclusive, and h is an integer from 1 to 5 inclusive.

Among the oxyalkylene group and polyoxyalkylene group represented by the following formula (21), preferable ones are those in which f is equal to 1, g is an integer of from 3 to 70, and h is 2 or 3. Those in which h is 2 or 3 may be linked in blocks or at random, and the same applies to other cases where h is an integer other than 2 or 3.

Typically, the amino-modified silicone polymers are represented by the following formulas (22) or (23):

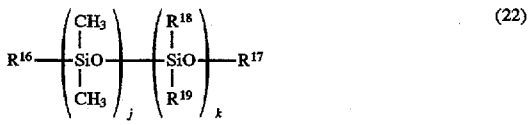 (22)

wherein $R^{16}$ represents methyl or hydroxy, $R^{17}$ represents methyl or hydrogen, $R^{18}$ represents the aforementioned aminoalkyl (formula (19) or (20)), $R^{19}$ represents hydroxy, hydroxyalkyl, oxyalkylene, or polyoxyalkylene, and j and k are integers which vary depending on the molecular weight.

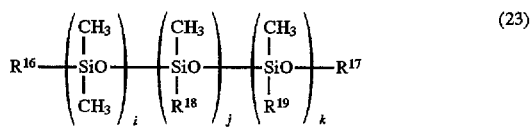

wherein $R^{16}$, $R^{17}$, $R^{18}$, and $R^{19}$ have the same meaning as defined above, and i, j, and k are integers which vary depending on the molecular weight.

Of the above-mentioned amino-modified silicone polymers, particularly preferable ones are those represented by the following formula (24):

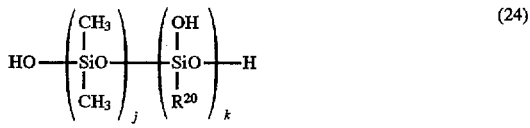

wherein $R^{20}$, j, and k have the same meaning as defined above.

Typical examples of the amino-modified silicone polymers in the present invention are those represented by the following formula (25) and having an average molecular weight of from about 3,000 to 100,000. This polymer is described in the aforementioned dictionary of CTFA (3rd ed.) under the name, Amodimethicone.

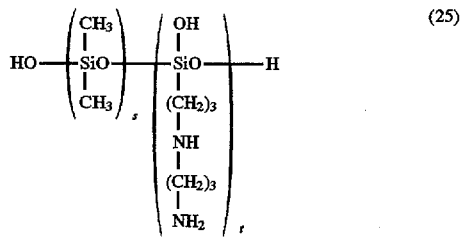

wherein s and t are integers which vary depending on the molecular weight ranging from 3,000 to 100,000.

The above-described cationic polymers are used singly or in combinations of two or more. They are preferably incorporated in an amount of from 0.05 to 10% based on the total amount of the composition. If the amount falls in a range of from 0.05 to 5%, particularly from 0.05 to 3%, an effect providing excellent feel to the touch of the hair is expected without impeding the firmness/elasticity-imparting effect and thus preferable.

The pH of the hair cosmetic composition of the present invention is preferably adjusted to fall in the range from 2 to 5, more preferably from 2.5 to 4.5, by adding thereto a compound capable of forming a buffer system such as an organic carboxylic acid or a salt thereof in order to allow the hair fibers sufficiently to swell for accelerating permeation of the firmness/elasticity-imparting components, naphthalenesulfonic acids and/or benzophenonesulfonic acids into the hair fibers.

The compounds which are capable of forming the buffer system include organic carboxylic acids such as citric acid, glycolic acid, succinic acid, tartaric acid, lactic acid, acetic acid, fumaric acid, malic acid, levulinic acid, butyric acid, valeric acid, oxalic acid, maleic acid, phthalic acid, mandelic acid, isethionic acid and their salts. Preferable salts of these carboxylic acids include sodium salts, potassium salts, and ammonium salts.

These carboxylic acids are used singly or in combinations of two or more. They are incorporated in such amounts that make the pH of the composition to fall within the above-indicated pH range. Generally, they are incorporated from 0.3 to 50%, especially from 0.5 to 30%, based on the total amount of the composition.

If necessary, the hair cosmetic composition of the present invention may further contain optional components as long as the effects of the invention are not impeded. The optional components include thickeners such as hydroxyethylcellulose, anionic, amphoteric, and other types of setting polymers, perfumes, pearl-hue imparting agents, colorants, UV absorbers, antioxidants, preservatives, etc. In order to further improve feel to the touch of the hair, it is possible to incorporate silicone derivatives such as dimethylpolysiloxanes, polyether-modified silicones, alkyl-modified silicones, alkoxy-modified silicones, and aliphatic modified silicones.

In the hair cosmetic composition of the present invention, the balance of the above-described components is water.

The hair cosmetic composition of the present invention can be prepared by a method generally known in the art into various products such as hair treatments, hair conditioners, and other products which are used outside the bath such as hair treatment foams, hair setting foams, hair sprays, and hair creams.

In use, the hair cosmetic composition of the present invention may, for example, be applied to hair fibers in the bath, be allowed to stand for 5 to 30 minutes, and then rinsed off. During the standing period, the hair may be heated to a suitable temperature which is preferably from 30° to 50° C. When the hair cosmetic composition of the invention is used outside the bath, it is applied to the hair (either dry hair or wet hair after shampooing) and is brought into full contact with the entire surfaces of the hair fibers.

EXAMPLES

The present invention will next be described by way of examples, which should not be construed as limiting the invention.

Examples 1 to 10 and Comparative Examples 1 to 8:

The hair cosmetic compositions shown in Tables 1, 2, 3, 4, and 5 were prepared, and the hair treatment effects of the compositions were investigated.

(1) The hair used in the test:

Hair fiber samples of Japanese women which had not undergone any beauty treatments such as cold perming or bleaching.

(2) Evaluation method:

Hair fiber samples each weighing 8 g were provided. Each sample was divide into two. To one half, an invention composition (or a comparative composition) in a solution of 1:1 was applied, and was allowed to stand at room temperature for 10 minutes. Subsequently, the composition was rinsed off with running water, after which the hair was dried with a hair drier or similar means. The resulting sample represented a treated sample. The other half, which was not treated with any compositions represented a non-treated sample. 10 expert panelists compared each pair in a side-by-side manner with respect to the firmness/elasticity, moistened feel to the touch of the hair, and smoothness to the touch of the hair. The evaluation of firmness/elasticity was repeated after the sample was shampooed twice. The evaluation standards were as follows:

Firmness/elasticity of the hair:

A: Remarkably excellent firmness/elasticity
B: Good firmness/elasticity
C: Slightly better firmness/elasticity than untreated hair
D: The same level as that of untreated hair.

Moistened feel to the touch of the hair:

A: Very moistened feel

B: Fairly moistened feel
C: Slightly moistened feel
D: The same level as that of untreated hair.
Smoothness to the touch of the hair:
A: Very smooth
B: Fairly smooth
C: Slightly smooth
D: The same level as that of untreated hair.

TABLE 1

| Components (%) | Ex. 1 | Ex. 2 |
|---|---|---|
| (1) Benzyloxy ethanol | 4.0 | — |
| (2) Benzyl alcohol | — | 4.0 |
| (3) 95% 8-Acetylated sucrose-modified ethanol | 10.0 | 10.0 |
| (4) Propylene glycol | 3.0 | 3.0 |
| (5) 2-Naphthalenesulfonic acid | — | 2.0 |
| (6) Oxybenzonesulfonic acid*[1] | 2.0 | — |
| (7) N-Palm oil aliphatic acyl-L-glutamic acid triethanolamine (30%)*[2] | 8.0 | — |
| (8) 2-Alkyl-N-carboxymethyl-N-hydroxyethyl imidazolium betaine (58%)*[3] | — | 4.5 |
| (9) Cetanol | 5.0 | 4.0 |
| (10) Behenyl alcohol | — | 0.5 |
| (11) alpha-Monoisostearylglyceryl ether*[4] | 1.5 | 1.5 |
| (12) Polyoxyethylene cetyl ether (3 E.O.) | 2.0 | 2.0 |
| (13) Polyoxyethylene cetyl ether (40 E.O.) | 2.0 | 2.0 |
| (14) Hydroxyethylcellulose hydroxypropyl trimethylammonium chloride ether*[5] | — | — |
| (15) Dimethyldiallyl ammonium chloride . acrylic amide copolymer*[6] | — | — |
| (16) Aqueous citric acid solution (50%) | 1.0 | 0.5 |
| (17) NaOH (48%) | suitable amount | |
| (18) Purified water | balance | |
| pH (adjusted with NaOH) | 3.0 | 7.0 |

Firmness/elasticity (after dried):

| | | |
|---|---|---|
| Immediately after shampooing | A | B |
| After 2 shampooings | A | B |

Feel to the touch of the hair during rinsing:

| | | |
|---|---|---|
| Smoothness | B | B |
| Moistness | B | B |

Feel to the touch of the hair after drying:

| | | |
|---|---|---|
| Smoothness | A | A |
| Moistness | A | A |

TABLE 2

| Components (%) | Ex. 3 | Ex. 4 |
|---|---|---|
| (1) Benzyloxy ethanol | 4.0 | — |
| (2) Benzyl alcohol | — | 4.0 |
| (3) 95% 8-Acetylated sucrose-modified ethanol | 10.0 | 10.0 |
| (4) Propylene glycol | 4.5 | 4.5 |
| (5) 2-Naphthalenesulfonic acid | 1.0 | — |
| (6) Oxybenzonesulfonic acid*[1] | 1.0 | 2.0 |
| (7) N-Palm oil aliphatic acyl-L-glutamic acid triethanolamine (30%)*[2] | — | 8.0 |
| (8) 2-Alkyl-N-carboxymethyl-N-hydroxyethyl imidazolium betaine (58%)*[3] | 4.5 | — |
| (9) Cetanol | — | — |
| (10) Behenyl alcohol | — | — |
| (11) alpha-Monoisostearylglyceryl ether*[4] | 1.5 | 1.5 |
| (12) Polyoxyethylene cetyl ether (3 E.O.) | 2.0 | 2.0 |
| (13) Polyoxyethylene cetyl ether (40 E.O.) | 2.0 | 2.0 |
| (14) Hydroxyethylcellulose hydroxypropyl trimethylammonium chloride ether*[5] | — | — |
| (15) Dimethyldiallyl ammonium chloride . acrylic amide copolymer*[6] | — | — |
| (16) Aqueous citric acid solution (50%) | 1.0 | 0.5 |
| (17) NaOH (48%) | suitable amount | |
| (18) Purified water | balance | |
| pH (adjusted with NaOH) | 3.0 | 7.0 |

TABLE 2-continued

| Components (%) | Ex. 3 | Ex. 4 |
|---|---|---|

Firmness/elasticity (after dried):

| | | |
|---|---|---|
| Immediately after shampooing | A | B |
| After 2 shampooings | A | B |

Feel to the touch of the hair during rinsing:

| | | |
|---|---|---|
| Smoothness | B | B |
| Moistness | B | B |

Feel to the touch of the hair after drying:

| | | |
|---|---|---|
| Smoothness | B | B |
| Moistness | B | B |

TABLE 3

| Components (%) | Ex. 5 | Ex. 6 | Ex. 7 |
|---|---|---|---|
| (1) Benzyloxy ethanol | 4.0 | 4.0 | — |
| (2) Benzyl alcohol | — | — | 4.0 |
| (3) 95% 8-Acetylated sucrose-modified ethanol | 10.0 | 10.0 | 10.0 |
| (4) Propylene glycol | 3.0 | 3.0 | 3.0 |
| (5) 2-Naphthalenesulfonic acid | 1.0 | 1.0 | — |
| (6) Oxybenzonesulfonic acid*[1] | 1.0 | 1.0 | 2.0 |
| (7) N-Palm oil aliphatic acyl-L-glutamic acid triethanolamine (30%)*[2] | 8.0 | 8.0 | — |
| (8) 2-Alkyl-N-carboxymethyl-N-hydroxyethyl imidazolium betaine (58%)*[3] | — | — | 4.5 |
| (9) Cetanol | 5.0 | 5.0 | 4.0 |
| (10) Behenyl alcohol | — | — | 0.5 |
| (11) alpha-Monoisostearylglyceryl ether*[4] | 1.5 | 1.5 | 1.5 |
| (12) Polyoxyethylene cetyl ether (3 E.O.) | 2.0 | 2.0 | 2.0 |
| (13) Polyoxyethylene cetyl ether (40 E.O.) | 2.0 | 2.0 | 2.0 |
| (14) Hydroxyethylcellulose hydroxypropyl trimethylammonium chloride ether*[5] | 0.2 | — | 0.2 |
| (15) Dimethyldiallyl ammonium chloride . acrylic amide copolymer*[6] | 0.2 | — | 0.2 |
| (16) Imidazolium methochloride . vinyl pyrrolidone copolymer*[7] | — | 0.4 | — |
| (17) Aqueous citric acid solution (50%) | 1.0 | 1.0 | 1.0 |
| (18) NaOH (48%) | suitable amount | | |
| (19) Purified water | balance | | |
| pH (adjusted with NaOH) | 3.0 | 3.0 | 7.0 |

Firmness/elasticity (after dried):

| | | | |
|---|---|---|---|
| Immediately after shampooing | A | A | B |
| After 2 shampooings | A | A | B |

Feel to the touch of the hair during rinsing:

| | | | |
|---|---|---|---|
| Smoothness | A | B | A |
| Moistness | A | B | A |

Feel to the touch of the hair after drying:

| | | | |
|---|---|---|---|
| Smoothness | A | A | A |
| Moistness | A | A | A |

TABLE 4

| Components (%) | Ex. 8 | Ex. 9 | Ex. 10 |
|---|---|---|---|
| (1) Benzyloxy ethanol | 4.0 | 4.0 | — |
| (2) Benzyl alcohol | — | — | 4.0 |
| (3) 95% 8-Acetylated sucrose-modified ethanol | 10.0 | 10.0 | 10.0 |
| (4) Propylene glycol | 3.0 | 3.0 | 3.0 |
| (5) 2-Naphthalenesulfonic acid | 2.0 | 2.0 | — |
| (6) Oxybenzonesulfonic acid*[1] | — | — | 2.0 |
| (7) N-Palm oil aliphatic acyl-L-glutamic acid triethanolamine (30%)*[2] | — | — | 8.0 |
| (8) 2-Alkyl-N-carboxymethyl-N-hydroxyethyl imidazolium betaine (58%)*[3] | 4.5 | 4.5 | — |
| (9) Cetanol | — | — | — |
| (10) Behenyl alcohol | — | — | 0.5 |

TABLE 4-continued

| Components (%) | Ex. 8 | Ex. 9 | Ex. 10 |
|---|---|---|---|
| (11) alpha-Monoisostearylglyceryl ether*4 | 1.5 | 1.5 | 1.5 |
| (12) Polyoxyethylene cetyl ether (3 E.O.) | 2.0 | 2.0 | 2.0 |
| (13) Polyoxyethylene cetyl ether (40 E.O.) | 2.0 | 2.0 | 2.0 |
| (14) Hydroxyethylcellulose hydroxypropyl trimethylammonium chloride ether*5 | 0.2 | — | 0.2 |
| (15) Dimethyldiallyl ammonium chloride . acrylic amide copolymer*6 | 0.2 | — | 0.2 |
| (16) Imidazolium methochloride . vinyl pyrrolidone copolymer*7 | — | 0.4 | — |
| (17) Aqueous citric acid solution (50%) | 1.0 | 1.0 | 0.5 |
| (18) NaOH (48%) | | suitable amount | |
| (19) Purified water | | balance | |
| pH (adjusted with NaOH) | 3.0 | 3.0 | 7.0 |
| Firmness/elasticity (after dried): | | | |
| Immediately after shampooing | A | A | B |
| After 2 shampooings | A | A | B |
| Feel to the touch of the hair during rinsing: | | | |
| Smoothness | A | B | A |
| Moistness | A | B | A |
| Feel to the touch of the hair after drying: | | | |
| Smoothness | B | B | B |
| Moistness | B | B | B |

TABLE 5

| Components (%) | Comp. Ex. 1 | Comp. Ex. 2 |
|---|---|---|
| (1) Benzyloxy ethanol | — | — |
| (2) Benzyl alcohol | — | 4.0 |
| (3) 95% 8-Acetylated sucrose-modified ethanol | — | 10.0 |
| (4) Propylene glycol | — | 3.0 |
| (5) 2-Naphthalenesulfonic acid | — | — |
| (6) Oxybenzonesulfonic acid*1 | 2.0 | — |
| (7) N-Palm oil aliphatic acyl-L-glutamic acid triethanolamine (30%)*2 | 8.0 | — |
| (8) 2-Alkyl-N-carboxymethyl-N-hydroxyethyl imidazolium betaine (58%)*3 | — | 4.5 |
| (9) Cetanol | 5.0 | 4.0 |
| (10) Behenyl alcohol | — | 0.5 |
| (11) alpha-Monoisostearylglyceryl ether*4 | 1.5 | 1.5 |
| (12) Polyoxyethylene cetyl ether (3 E.O.) | 2.0 | 2.0 |
| (13) Polyoxyethylene cetyl ether (40 E.O.) | 2.0 | 2.0 |
| (14) Hydroxyethylcellulose hydroxypropyl trimethylammonium chloride ether*5 | — | — |
| (15) Dimethyldiallyl ammonium chloride . acrylic amide copolymer*6 | — | — |
| (16) Aqueous citric acid solution (50%) | 1.0 | 1.0 |
| (17) NaOH (48%) | | suitable amount |
| (18) Purified water | | balance |
| pH (adjusted with NaOH) | 3.0 | 3.0 |
| Firmness/elasticity (after dried): | | |
| Immediately after shampooing | C | D |
| After 2 shampooings | D | D |
| Feel to the touch of the hair during rinsing: | | |
| Smoothness | B | B |
| Moistness | B | B |
| Feel to the touch of the hair after drying: | | |
| Smoothness | B | B |
| Moistness | B | B |

TABLE 6

| Components (%) | Comp. Ex. 3 | Comp. Ex. 4 |
|---|---|---|
| (1) Benzyloxy ethanol | — | — |
| (2) Benzyl alcohol | 4.0 | 4.0 |
| (3) 95% 8-Acetylated sucrose-modified ethanol | 10.0 | 10.0 |
| (4) Propylene glycol | 3.0 | 4.5 |
| (5) 2-Naphthalenesulfonic acid | — | — |
| (6) Oxybenzonesulfonic acid*1 | 2.0 | 2.0 |
| (7) N-Palm oil aliphatic acyl-L-glutamic acid triethanolamine (30%)*2 | — | 8.0 |
| (8) 2-Alkyl-N-carboxymethyl-N-hydroxyethyl imidazolium betaine (58%)*3 | — | — |
| (9) Cetanol | 5.0 | — |
| (10) Behenyl alcohol | — | — |
| (11) alpha-Monoisostearylglyceryl ether*4 | 1.5 | — |
| (12) Polyoxyethylene cetyl ether (3 E.O.) | 2.0 | — |
| (13) Polyoxyethylene cetyl ether (40 E.O.) | 2.0 | — |
| (14) Hydroxyethylcellulose hydroxypropyl trimethylammonium chloride ether*5 | — | — |
| (15) Dimethyldiallyl ammonium chloride . acrylic amide copolymer*6 | — | — |
| (16) Aqueous citric acid solution (50%) | 1.0 | 1.0 |
| (17) NaOH (48%) | | suitable amount |
| (18) Purified water | | balance |
| pH (adjusted with NaOH) | 3.0 | 3.0 |
| Firmness/elasticity (after dried): | | |
| Immediately after shampooing | A | A |
| After 2 shampooings | A | A |
| Feel to the touch of the hair during rinsing: | | |
| Smoothness | D | C |
| Moistness | C | D |
| Feel to the touch of the hair after drying: | | |
| Smoothness | D | C |
| Moistness | C | D |

TABLE 7

| Components (%) | Comp. Ex. 5 | Comp. Ex. 6 |
|---|---|---|
| (1) Benzyloxy ethanol | — | — |
| (2) Benzyl alcohol | — | 4.0 |
| (3) 95% 8-Acetylated sucrose-modified ethanol | — | 10.0 |
| (4) Propylene glycol | — | 3.0 |
| (5) 2-Naphthalenesulfonic acid | — | — |
| (6) Oxybenzonesulfonic acid*1 | 2.0 | — |
| (7) N-Palm oil aliphatic acyl-L-glutamic acid triethanolamine (30%)*2 | 8.0 | — |
| (8) 2-Alkyl-N-carboxymethyl-N-hydroxyethyl imidazolium betaine (58%)*3 | — | 4.5 |
| (9) Cetanol | 5.0 | 4.0 |
| (10) Behenyl alcohol | — | 0.5 |
| (11) alpha-Monoisostearylglyceryl ether*4 | 1.5 | 1.5 |
| (12) Polyoxyethylene cetyl ether (3 E.O.) | 2.0 | 2.0 |
| (13) Polyoxyethylene cetyl ether (40 E.O.) | 2.0 | 2.0 |
| (14) Hydroxyethylcellulose hydroxypropyl trimethylammonium chloride ether*5 | 2.0 | 2.0 |
| (15) Dimethyldiallyl ammonium chloride . acrylic amide copolymer*6 | 0.2 | 0.2 |
| (16) Aqueous citric acid solution (50%) | 1.0 | 0.5 |
| (17) NaOH (48%) | | suitable amount |
| (18) Purified water | | balance |
| pH (adjusted with NaOH) | 3.0 | 3.0 |
| Firmness/elasticity (after dried): | | |
| Immediately after shampooing | C | D |
| After 2 shampooings | D | D |
| Feel to the touch of the hair during rinsing: | | |
| Smoothness | A | A |

TABLE 7-continued

| Components (%) | Comp. Ex. 5 | Comp. Ex. 6 |
|---|---|---|
| Moistness | A | A |
| Feel to the touch of the hair after drying: | | |
| Smoothness | A | A |
| Moistness | A | A |

TABLE 8

| Components (%) | Comp. Ex. 7 | Comp. Ex. 8 |
|---|---|---|
| (1) Benzyloxy ethanol | — | — |
| (2) Benzyl alcohol | 4.0 | 4.0 |
| (3) 95% 8-Acetylated sucrose-modified ethanol | 10.0 | 10.0 |
| (4) Propylene glycol | 3.0 | 4.5 |
| (5) 2-Naphthalenesulfonic acid | — | — |
| (6) Oxybenzonesulfonic acid*1 | 2.0 | 2.0 |
| (7) N-Palm oil aliphatic acyl-L-glutamic acid triethanolamine (30%)*2 | — | 8.0 |
| (8) 2-Alkyl-N-carboxymethyl-N-hydroxyethyl imidazolium betaine (58%)*3 | — | — |
| (9) Cetanol | 5.0 | — |
| (10) Behenyl alcohol | — | — |
| (11) alpha-Monoisostearylglyceryl ether*4 | 1.5 | — |
| (12) Polyoxyethylene cetyl ether (3 E.O.) | 2.0 | — |
| (13) Polyoxyethylene cetyl ether (40 E.O.) | 2.0 | — |
| (14) Hydroxyethylcellulose hydroxypropyl trimethylammonium chloride ether*5 | 0.2 | 0.2 |
| (15) Dimethyldiallyl ammonium chloride . acrylic amide copolymer*6 | 0.2 | 0.2 |
| (16) Aqueous citric acid solution (50%) | 1.0 | 0.5 |
| (17) NaOH (48%) | suitable amount | |
| (18) Purified water | balance | |
| pH (adjusted with NaOH) | 3.0 | 3.0 |
| Firmness/elasticity (after dried): | | |
| Immediately after shampooing | A | A |
| After 2 shampooings | A | A |
| Feel to the touch of the hair during rinsing: | | |
| Smoothness | D | C |
| Moistness | C | D |
| Feel to the touch of the hair after drying: | | |
| Smoothness | C | C |
| Moistness | C | C |

Note)
*1: Uvinul MS-40 (BASF JAPAN)
*2: Amisoft CT12 (Ajinomoto)
*3: Amphitol 20Y (Kao)
*4: GE-1S (Kao)
*5: Polymer-JR400 (Union Carbide)
*6: Merquat 2200 (Calgon)
*7: Luviquat FC (BASF)

EXAMPLE 11

A hair treatment composition of the following formula was prepared by a routine method. It had excellent properties in both the firmness/elasticity of hair fibers and the conditioning effects (moistness, smoothness).

| Formula | (%) |
|---|---|
| (1) 2-Naphthalenesulfonic acid . Na | 1.0 |
| (2) Oxybenzonesulfonic acid | 1.0 |
| (3) 95% 8-Acetylated sucrose-modified ethanol | 10.0 |
| (4) Benzyloxy ethanol | 3.0 |
| (5) Dimethyldiallyl ammonium chloride . acrylic amide copolymer | 0.3 |
| (6) Hydroxyethylcellulose hydroxypropyl-trimethylammonium chloride ether | 0.3 |
| (7) Aqueous citric acid solution (50%) | 1.0 |
| (8) N-Palm oil aliphatic acyl-L-glutamic acid triethanolamine*1 | 3.0 |
| (9) Monolauryl phosphoric acid*2 | 2.5 |
| (10) Cetanol | 5.0 |
| (11) Polyoxyethylene cetyl ether (40 E.O.) | 2.0 |
| (12) Aqueous NaOH solution (48%) | suitable amount for adjusting pH to 3.0 |
| (13) Purified water | balance |
| Total | 100 |

Note)
*1: Amisoft LS-11 (Ajinomoto)
*2: MAP-20H (Kao)

EXAMPLE 12

A hair treatment composition of the following formula was prepared by a routine method. It had excellent properties in both the firmness/elasticity of hair fibers and the conditioning effects.

| Formula | (%) |
|---|---|
| (1) 1-Naphthalenesulfonic acid . Na | 2.0 |
| (2) 95% 8-Acetylated sucrose-modified ethanol | 5.0 |
| (3) Diethylene glycol monoethyl ether | 5.0 |
| (4) Benzyl alcohol | 4.0 |
| (5) Hydroxyethylcellulose hydroxypropyl-trimethylammonium chloride ether | 0.5 |
| (6) Aqueous citric acid solution (50%) | 1.0 |
| (7) Lauryldimethylamine oxide (35%)*1 | 1.0 |
| (8) Amideamino acid triethanolamine (34%)*2 | 5.0 |
| (9) Cetanol | 4.0 |
| (10) Behenyl alcohol | 1.5 |
| (11) Polyoxyethylene cetyl ether (40 E.O.) | 2.0 |
| (12) Aqueous NaOH solution (48%) | suitable amount for adjusting pH to 3.5 |
| (13) Purified water | balance |
| Total | 100 |

Note)
*1: Amphitol 20N (Kao)
*2: Amphitol 20Y-N (Kao)

EXAMPLE 13

A hair foam composition of the following formula was prepared by a routine method. It had excellent properties in both the firmness/elasticity of hair fibers and the conditioning effects (moistness, smoothness).

| Formula | (%) |
|---|---|
| (1) Oxybenzonesulfonic acid | 0.5 |
| (2) 95% 8-Acetylated sucrose-modified ethanol | 10.0 |
| (3) Amideamino acid triethanolamine 24% (= Amphitol 20Y-N (Kao)) | 0.5 |
| (4) Polyoxyethylene-sec-tetradecyl ether (9 E.O.)*1 | 1.0 |
| (5) N-methacryloylethyl-N,N-dimethyl- | 1.0 |

19
-continued

| Formula | (%) |
|---|---|
| ammonium . alpha-N-methylcarboxybetaine . butyl methacrylate copolymer*² | |
| (6) Dimethylethylene chloride piperidium copolymer*³ | 0.1 |
| (7) Octyl dodecanol*⁴ | 0.5 |
| (8) Propylene glycol | 1.0 |
| (9) Aqueous NaOH solution (48%) | suitable amount for adjusting pH to 3.5 |
| (10) Purified water | balance |
| (11) Propellant (LPG 4.5 kg) | 7.0 |
| Total | 100 |

Note)
*1: Softanol 90 (Kao)
*2: Yukaformer (Mitsubishi Petrochemical)
*3: Merquat 100 (Merck)
*4: Kalcohl 200GD (Kao)

EXAMPLE 14

A hair foam composition of the following formula was prepared by a routine method. It had excellent properties in both the firmness/elasticity of hair fibers and the conditioning effects.

| Formula | (%) |
|---|---|
| (1) 2-Naphthalenesulfonic acid . Na | 0.5 |
| (2) 95% 8-Acetylated sucrose-modified ethanol | 10.0 |
| (3) Benzyl alcohol | 0.5 |
| (5) Amideamino acid triethanolamine (34%) | 0.5 |
| (6) Polyoxyethylene-sec-tetradecyl ether (9 E.O.) | 0.5 |
| (7) Octyl dodecanol | 0.5 |
| (8) Propylene glycol | 1.0 |
| (9) Lauryl acrylate . vinyl acetate copolymer dispersion (20%)*¹ | 4.0 |
| (10) Vinylpyrrolidone . N,N-dimethylaminoethyl methacrylic acid copolymer, diethyl sulfate*² | 2.5 |
| (11) Aqueous NaOH solution (48%) | suitable amount for adjusting pH to 3.5 |
| (13) Purified water | balance |
| (14) Propellant (LPG 4.5 kg) | 7.0 |
| Total | 100 |

Note)
*1: Polymer ND (Kao)
*2: Gafquat 755N (ISP)

Industrial Utility

The hair cosmetic composition according to the present invention imparts satisfactory firmness/elasticity to hair fibers in a short time, holds the firmness/elasticity for a long time, and provides the hair fibers with excellent conditioning effects.

We claim:

1. A hair cosmetic composition which comprises the following components (A), (B), (C), and (D):

(A) an organic solvent,
   (B) a naphthalene sulfonic acid and/or a benzophenone sulfonic acid,
   (C) an anionic surfactant and/or an amphoteric surfactant, and
   (D) an oily agent, wherein the amounts of the components (A), (B), (C), and (D) are 0.5 to 50% by weight, 0.1 to 10% by weight, 0.1 to 25% by weight, and 1 to 25% by weight based on the total weight of the composition, respectively.

2. The hair cosmetic composition according to claim 1, wherein the component (A) is selected from the group consisting of alkylpyrrolidones having C1-C18 N-alkyl, C1-C4 alkylene carbonates, and the alcohols represented by the following formula (1):

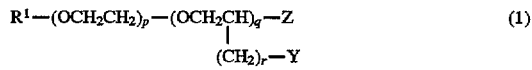

wherein $R^1$ represents hydrogen, C1-C4 alkyl, or a group

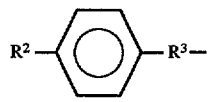

(wherein $R^2$ represents hydrogen, methyl, or methoxy, $R^3$ represents a direct bond or a C1-C3 saturated or unsaturated divalent hydrocarbon group), Y and Z each represents hydrogen or hydroxy, p, q, and r are integers of from 0 to 5, with the exception of the cases where $p=q=r=0$ and $Z=H$; and $p=q=r=0$, $R^1=H$, and $Z=OH$.

3. The hair cosmetic composition according to claim 1, wherein the component (A) is represented by the following formula (3):

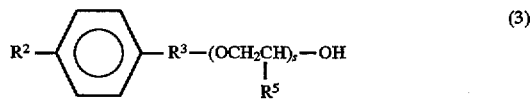

wherein $R^2$ is hydrogen, methyl, or methoxy, $R^3$ is a direct bond or a C1-C3 saturated or unsaturated divalent hydrocarbon group, $R^5$ is hydrogen or methyl, s is an integer of from 0 to 5, provided that $R^3$ is not a direct bond if s is 0.

4. The hair cosmetic composition according to claim 1, wherein the component D is selected from the group consisting of C12-C30 saturated alcohols, C12-C30 unsaturated alcohols, ethers of these alcohols with polyhydric alcohols, esters of said alcohols with C1-C11 fatty acids, C12-C30 saturated fatty acids, C12-C30 unsaturated fatty acids esters of these fatty acids and monohydric alcohols, esters of these fatty acids and alcohols, amides of said fatty acids and amines, sterols, squalenes, phospholipids, glycolipids, oils and fats of animal and vegetable origin, and hydrocarbons.

5. The hair cosmetic composition according to claim 1, wherein the component (D) is a higher alcohol having C12-C26 linear or branched alkyl or alkenyl.

6. The hair cosmetic composition according to claim 1, which further comprises a cationic polymer.

7. The hair cosmetic composition according to claim 6, wherein the cationic polymer is selected from the group consisting of polymers having a unit structure of dimethyldiallylammonium chloride and copolymers thereof, polymers having a unit structure of methacrylamide alkyl trimethyl ammonium and copolymers thereof, cationic cellulose, and amino-modified silicone polymers.

8. The hair cosmetic composition according to claim 6, wherein the cationic polymer is selected from the group consisting of a polymer of dimethyldiallyl ammonium chloride, a copolymer of dimethyldiallylammonium chloride with acrylate, a copolymer of dimethyldiallyl ammonium chloride with acrylic amide, a three component-copolymer of dimethyldiallylammonium chloride/acrylic amide/acrylate, a copolymer of dimethyldiallylammonium chloride with hydroxyethylcellulose, a polymer of methacrylamide propyl trimethyl ammonium, a copolymer of methacrylamide propyl trimethyl ammonium with vinyl pyrrolidone, a copolymer of dimethylaminoethyl methacrylate with vinyl pyrrolidone, and hydroxyethylcellulose-2-hydroxypropyl triethylammonium chloride ether.

9. The hair cosmetic composition according to claim 1, wherein the pH of the composition is adjusted to fall within a range of from 2 to 5 with a compound capable of forming a buffer system.

10. The hair composition according to claim 1, wherein:
(A) is present in an amount of 2 to 30% by weight;
(B) is present in an amount of 0.5 to 5% by weight;
(C) is present in an amount of 1.0 to 10% by weight; and
(D) is present in an amount of 3 to 20% by weight;
said % by weight being based on the total weight of the composition.

11. The hair composition according to claim 1, wherein:
(A) is present in an amount of 5 to 25% by weight;
(B) is present in an amount of 1.0 to 3.0% by weight;
(C) is present in an amount of 1.0 to 10% by weight; and
(D) is present in an amount of 5 to 15% by weight;
said % by weight being based on the total weight of the composition.

* * * * *

UNITED STATES PATENT AND TRADEMARK OFFICE
CERTIFICATE OF CORRECTION

PATENT NO. : 5,683,685
DATED : NOVEMBER 4, 1997
INVENTOR(S) : YUJI HIRANO, ET AL.

It is certified that error appears in the above-identified patent and that said Letters Patent is hereby corrected as shown below:

Column 20, line 39, "fatty acids esters"

should read --fatty acids, esters--.

Signed and Sealed this

Seventh Day of July, 1998

*Attest:*

BRUCE LEHMAN

*Attesting Officer*     Commissioner of Patents and Trademarks